US007556932B2

(12) United States Patent
Cheng et al.

(10) Patent No.: US 7,556,932 B2
(45) Date of Patent: Jul. 7, 2009

(54) PARTICLE BASED HOMOGENEOUS ASSAYS USING CAPILLARY ELECTROPHORESIS WITH LASER-INDUCED FLUORESCENCE DETECTION

(75) Inventors: Anthony K. Cheng, Anaheim, CA (US); Julie S. Kim, Placentia, CA (US); Chan S. Oh, Chino Hills, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 11/611,072

(22) Filed: Dec. 14, 2006

(65) Prior Publication Data

US 2007/0259338 A1 Nov. 8, 2007

Related U.S. Application Data

(62) Division of application No. 09/947,990, filed on Sep. 6, 2001, now Pat. No. 7,179,658.

(51) Int. Cl.
*G01N 33/00* (2006.01)
(52) U.S. Cl. ............... 435/7.94; 435/7.1; 435/7.92; 436/172; 436/518; 436/524; 204/451
(58) Field of Classification Search ............ 435/6, 435/7.1, 7.92, 7.94; 436/164, 172, 501, 518, 436/524, 800; 204/451
See application file for complete search history.

(56) References Cited

U.S. PATENT DOCUMENTS 5,185,243 A 2/1993 Ullman et al.

| 5,434,088 A | 7/1995 | Ikeda et al. |
| 5,571,680 A | 11/1996 | Chen |
| 5,863,401 A | 1/1999 | Chen |
| 6,103,537 A | 8/2000 | Ullman et al. |

FOREIGN PATENT DOCUMENTS

| EP | 0 848 251 A2 | 6/1998 |
| WO | WO 00/79260 A | 12/2000 |

OTHER PUBLICATIONS

Paquette, et al., "Detection of specific antibodies using immunosubtraction and capillary electrophoresis instrumentation", Electrophoresis, Weinheim, DE, vol. 22, No. 12, Aug. 2001, pp. 2391-2397, XP-002286281.

Wang, et al., "Noncompetitive immunoassays using protein G affinity capillary chromatography and capillary electrophoresis with laser-induced fluorescence detection", Journal of Chromatography, Elsevier Science Publishers B. V. Amsterdam, NL, vol. 848, No. 1-2, Jul. 2, 1999, pp. 139-1148, XP004184207.

*Primary Examiner*—Gailene R Gabel
*Assistant Examiner*—Gary W Counts
(74) *Attorney, Agent, or Firm*—Jeffry K. Russell (57) ABSTRACT

The invention provides highly sensitive and rapid homogeneous assays which employ particle-enhanced assay formats in concert with capillary electrophoresis and laser-induced fluorescence (LIF) detection to determine the concentration of an analyte of interest in a sample. Such a determination is made by measuring fluorescent signal(s) (i.e., an electropherogram) produced upon LIF of species present in the reaction mixture that are capable of producing such signals. The method of this invention produces simplified electropherograms by reducing the number of signals that must be separated and subsequently measured, and therefore increases the accuracy of the detection and/or quantification of target analyte concentration in a sample.

10 Claims, 3 Drawing Sheets

Figure 1. Quantitation of avidin on latex particle at fixed biotin-fluorescein concentration by CE-LIF: latex-avidin A/C ratio 0.35; biotin-fluorescein, $3 \times 10^{-7}$ M; latex-avidin dilutions from neat to 1:20.

Figure 2. Quantitation of avidin on latex particle at fixed latex-avidin concentration by CE-LIF: latex-avidin dilution 1:100; biotin-fluorescein concentrations, $9 \times 10^{-9}$ M to $3 \times 10^{-7}$ M.

Figure 3. Quantitation and comparison of two latex-avidin lots by CE-LIF: latex-avidin A/C ratio 0.15; latex-avidin lots, 365R and KP1; latex-avidin dilutions, 1:20 to 1:100; biotin-fluoroscein 3.68 x$10^{-8}$ M.

PARTICLE BASED HOMOGENEOUS ASSAYS USING CAPILLARY ELECTROPHORESIS WITH LASER-INDUCED FLUORESCENCE DETECTION

RELATED APPLICATION

This application is a divisional application of U.S. patent application Ser. No. 09/947,990, filed on Sept. 6, 2001, now U. S. Pat. No. 7,179,658, the content of which is incorporated herein by reference in its entirety.

FIELD OF THE INVENTION

The invention relates generally to assays for the detection of analytes in a sample, and specifically to a novel particle-based homogeneous assays using capillary electrophoresis with laser-induced fluorescence detection.

BACKGROUND OF THE INVENTION

The ability to detect and/or quantitate the concentration of a pharmacological agent, metabolite, or toxin is a central aspect of modern diagnosis and management of disease. In some cases, such analytes can be detected directly by assaying their biological activities. In most cases, however, it is more efficient to detect such molecules by virtue of their capacity to specifically bind to antibodies, or by their physical characteristics, such as electrophoretic mobility.

Assays for the detection of target analytes involve the use of a binding partner which specifically binds to the analyte of interest in a sample to aid in the detection of the analyte. One type of assay for the detection of a target analytes are immunoassays. Immunoassays are assay systems that exploit the ability of an antibody to specifically recognize and bind to a particular target analyte. The concept of immunoassays is based on a specific chemical reaction between an antibody and its corresponding antigen. Quantitation involves the separation of an antibody-bound antigen from the free antigen followed by the detection of an antibody-bound antigen or free antigen in solution, depending upon the specific analytical scheme. Such assays are used extensively in modern diagnostics (e.g., Fackrell, J., *Clin. Immunoassay* 8:213-219 (1985); Yolken, R. H., *Rev. Infect. Dis.* 4:35 (1982); Collins, W. P., In: Alternative Immunoassays, John Wiley & Sons, NY (1985); Ngo, T. T., et al., In: Enzyme Mediated Immunoassay, Plenum Press, NY (1985)).

There are many variations of assays for the detection of analytes, and the critical steps are either physical separation or discrimination and detection. Assays that require physical separation are termed "heterogeneous assays." In contrast, homogeneous assays are designed such that the removal of bound from unbound species is unnecessary. Because homogeneous assays lack a separation step and are more easily automated, they are more desirable than heterogeneous assays in applications that entail the screening of large numbers of patients.

Analytes present at concentration levels below $10^{-9}$ M are-generally assayed using either a competitive method or a direct method. In a competitive assay, the antigen of interest competes with a labeled antigen for a judicious amount of antibody. A direct assay is typically a sandwich assay involving two antibodies binding to different antigenic sites of an antigen. One antibody is bound to a solid phase material and is employed to harvest the antigen. The other antibody is labeled and used to generate quantitative information from the bound antigen (Cone, E. J., et al., *J. Forens. Sci.* 35:786-781 (1990); Baugh, L. D., et al., *J. Forens. Sci.* 36:79-85 (1991); Standefer, J. C., et al., *Clin. Chem.* 37:733-738 (1991)).

In order to facilitate the detection of binding between the analyte of interest and its binding partner, one or more reaction analytes is typically labeled (e.g., with a radioisotope, an enzyme, a fluorescent moiety, a chemiluminescent moiety, or a macroscopic label, such as a bead, etc.) (See Chard, T. et al., In: Laboratory Techniques and Biochemistry in Molecular Biology (Work, T. S., Ed.), North Holland Publishing Company, N.Y. (1978); Kemeny, D. M. et al. (Eds.), ELISA and Other Solid Phase Immunoassays, John Wiley & Sons, N.Y. (1988)). Radioisotopes have long been used in immunoassays. O'Leary, T. D. et al., for example, describe a radioimmunoassay for digoxin serum concentrations (O'Leary, T. D. et al., *Clin. Chem.* 25:332-334 (1979)). The difficulty of handling such hazardous materials and the problem of radioactive decay have led to the development of immunoassays that use other labels.

Fluorescent moieties are frequently used as labels in immunoassay formats (See Ichinose, N. et al., In: Fluorometric Analysis in Biomedical Chemistry, Vol. 10 (110), Chemical Analysis (Winefordner, J. D. et al., Eds.) John Wiley & Sons, NY (1991)). For example, a fluorescence polarization immunoassay format for cocaine has been described (TDx®, Abbott Laboratories, Inc.) The TDx® format has also been used to assay acetaminophen serum levels (Koizumi, F. et al., *Tohoku J. Exper. Med.* 155:159-(1988); Edinboro, L. E. et al., *Clin. Toxicol.* 29:241-(1991); Okurodudu, A. O. et al., *Clin. Chem.* 38:1040 (1992)), and serum digoxin levels (Okarodudu, A. O. et al., *Clin. Chem.* 38:1040 (1992)). Wong, S. H. Y. et al., have described the use of an automated (OPUS) analyzer to measure the digoxin concentration in a monoclonal antibody mediated, fluorescence-based assay protocol (Wong, S. H. Y. et al., *Clin. Chem.* 38:996 (1992)). Lee, D. H. et al. also disclose the use of a fluorescence polarization assay and a chemiluminescent assay format to assay digoxin levels (Lee, D. H. et al., *Clin. Chem.* 36:1121 (1990)).

Electrophoretic methods have also been used to facilitate the detection of target analytes. Such methods exploit the fact that molecules in solution have an intrinsic electrical charge. Thus, in the presence of an electric field, each molecular species migrates with a characteristic "electrophoretic" mobility which is dependent upon the mass to charge the ratio of the molecular species. When this ratio is different from among the various species present, they separate from one another. Under the influence of such a field, all of the variants will move toward a designated charge opposite to the charge of the variants; those having a lower electrophoretic mobility will move slower than, and hence be separated from, those having a (relative) higher electrophoretic mobility.

Electrophoresis has been used for the separation and analysis of mixtures. Electrophoresis involves the migration and separation of molecules in an electric field based on differences in mobility. Various forms of electrophoresis are known, including free zone electrophoresis, gel electrophoresis, isoelectric focusing, and isotachophoresis. One approach to immunoassays employs capillary electrophoresis (CE) for the separation of free and bound label. In general, CE involves introducing a sample into a capillary tube, i.e., a tube having an internal diameter of from about 2 µm to about 2000 µm (preferably, less than about 50 µm; most preferably, about 25 µm or less) and applying an electric field to the tube (Chen, F-T. A., *J. Chromatogr.* 516:69-78 (1991); Chen, F-T. A., et al., *J. Chromatogr.* 15:1143-1161 (1992)). Since each of the sample constituents has its own individual electrophoretic mobility, those having greater mobility travel through the capillary tube faster than those with slower mobility. Hence, the constituents of the sample are resolved into discrete zones in the capillary tube during their migration through the tube. (Heegard, N. H. H., et al., *Anal. Chem.* 64:2479-2482 (1992); Gordon, M. J., et al., *Anal. Chem.* 63:69-72 (1991); F-T. A., U.S. Pat. No. 5,202,006; Chen, F-T. A., U.S. Pat. No. 5,120,413; Hsieh, Y-Z., et al., U.S. Pat. No. 5,145,567). The method is well suited to automation, since it provides convenient on-line injection, detection, and real-time data analysis. Capillary electrophoresis may be used to separate an antibody-antigen complex from either the unbound form of the antigen or the antibody. Either the bound or free species may be analyzed and quantitated. U.S. Pat. No. 5,863,401 to Chen discloses a method for the simultaneous quantification of multiple drug analytes in urine, based on combining immunochemical binding with capillary electrophoretic separation and laser-induced fluorescence.

Although sandwich-specific binding assays can provide a much higher sensitivity than competitive assays, the heterogeneity of labeled receptors and antibodies makes the capillary electroseparation difficult to carry out. This results because the unbound and complexed form of the receptor migrates non-uniformly, thus producing broad, poorly defined, rather than sharp, well-defined, distributions upon electroseparation analysis. Thus, conventional electroseparation methods may not offer significant advantages for specific binding assay applications.

Various approaches have been disclosed to overcome the inhomogeneity of large biomolecules. In one approach, the electrophoretic mobility of a labeled antibody is tailored by attaching charged groups to the same labeled molecule. In another approach, one antibody is labeled and the other is highly charged by means of a charge modifying moiety attached to the antibody.

U.S. Pat. No. 5,571,680 to Chen discloses a method of effecting the separation of an antigen or antibody from an antigen-antibody complex by CE by modulating the electrophoretic mobility of the antigen or antibody by chemical modification with well-defined charge-bearing organic molecules, such as oligonucleotides.

U.S. Pat. No. 6,103,537 to Ullman et al. discloses a method for masking inhomogeneity of an antibody in assay mixtures that are to be separated by CE. The method involves preparing labeled reagent particles comprising a labeled analyte-specific antibody bound to insoluble particles, and incubating the sample containing an analyte of interest with the particle-bound antibodies to form a complex between the analyte and the labeled particle-bound antibody. The reaction mixture is separated by CE, and the labeled complex is detected to determine the concentration of the analyte. However, it is well known that in the preparation of such labeled reagent particles, it is impossible to control the amount of antibody that becomes bound to the insoluble particle. As a result, different particles will contain different amounts of immobilized antibody relative to the other particles and will therefore bind to different amounts of analyte. Consequently, the various labeled complexes formed between the reagent particles and the analyte in the sample will naturally be inhomogeneous and the signal detected from the labeled complexes will be broad. Therefore, it will be more difficult to accurately correlate with the concentration of the analyte, as well as to cleanly separate the complexed label from the free label.

Reagent particles comprising latex particles coated with avidin (latex-avidin) are key intermediates in the manufacturing of latex-avidin-bidentate reagents for the Synchron CX®, Synchron LX®, and Immage® systems of Beckman Coulter (U.S. Pat. Nos. 5,747,352; 5,422,281; and 5,196,351). However, there exists no in-process testing of the latex-avidin intermediate, because reliable direct methods are not available. Further, currently available methods are only applicable for analyzing free avidin in solution rather than assessing the concentration of avidin that is coated on the latex particle. Without knowledge of the avidin loading on the latex particles and consistency with previous lots, a general practice is to simply proceed to the next and final step by coupling the latex-avidin intermediate with the bidentate reagent to produce the latex-avidin-bidentate reagent. Since the bidentate coupling step is a simple and reliable one, failure in manufacturing the latex-avidin-bidentate reagent is then attributed to the latex-avidin material. When failure occurs, the bidentate reagent is wasted, the latex-avidin material has to be disposed of, a large amount of washing buffer is consumed, and most importantly, time is wasted. A common method to qualify the in-process latex-avidin intermediate is to couple a small amount of the latex-avidin material to a small quantity of the bidentate material, followed by immnunoreactivity assessment of the resulting conjugate reagent on Synchron CX® for its acceptability. This method, however, is labor intensive and time-consuming, requiring three to ten days to obtain the results. Thus, there is still a need for a simple, fast, and reliable method for the in-process testing of latex-avidin intermediates.

In view of the importance of accurately detecting and quantitating analytes in samples, it would be desirable to provide processes which combine the advantages of particle-enhanced assays, capillary electrophoresis, and fluorescent detection techniques to rapidly detect target analytes in a test sample. In particular, it would be desirable to provide processes for more accurately analyzing samples for analytes of interest using particle-enhanced assay procedures and capillary electrophoresis detection techniques. The present invention provides such methods.

SUMMARY OF THE INVENTION

The present invention provides highly sensitive and rapid homogeneous assays which employ particle-enhanced assay formats in concert with capillary electrophoresis and laser-induced fluorescence (LIF) detection to determine the concentration of an analyte of interest in a sample. Such a determination is made by measuring fluorescent signal(s), i.e., an electropherogram, produced upon the laser-induced fluorescence of species in the reaction mixture that is capable of producing such signals. Advantageously, the methods of this invention produce simplified electropherograms by reducing the number of signals that must be separated and subsequently measured, thus increasing the accuracy of the detection and/or quantification of target analyte concentration.

Accordingly, one aspect of this invention provides a competitive assay for determining the concentration of an analyte in a sample which comprises:
  (a) providing sensitized particles comprising an analyte-specific binding partner immobilized thereon;
  (b) providing a free fluorophore-labeled analyte comprising the analyte attached to a fluorescent moiety;
  (c) incubating the sample in the presence of a known amount of the sensitized particles and a known amount of fluorophore-labeled analyte under conditions that allow the formation of a first complex comprising the immobilized binding partner bound to the sample analyte and/or a second complex comprising the immobilized binding partner bound to the fluorophore-labeled analyte, whereby the fluorescence of the fluorophore moiety of the second complex is quenched upon the formation of the second complex;

(d) subjecting an amount of the incubated sample of step (c) to capillary electrophoresis; and (e) determining the concentration of an analyte by detecting a laser-induced fluorescence of the free fluorophore-labeled analyte, wherein the laser-induced fluorescence is directly proportional to the concentration of the analyte in the sample.

Another aspect of this invention provides a direct sandwich assay for determining the concentration of an analyte in a sample which comprises:

(a) providing sensitized particles comprising a first analyte-specific binding partner immobilized thereon;

(b) providing a free fluorophore-labeled binding partner comprising a second analyte-specific binding partner attached to a fluorescent moiety;

(c) incubating the sample with a known amount of the sensitized particles and a known amount of the fluorophore-labeled binding partner under conditions that allow the formation of a sandwich complex comprising the analyte bound to the immobilized first binding partner and to the labeled binding partner, whereby the fluorescence of the fluorophore moiety of the sandwich complex is quenched upon the formation of the complex;

(d) subjecting an amount of the incubated sample of step (c) to capillary electrophoresis; and (e) determining the concentration of the analyte by detecting a laser-induced fluorescence of the free fluorophore-labeled binding partner, wherein the laser-induced fluorescence is inversely proportional to the concentration of the analyte in the sample.

Particle-enhanced assays generally involve the use of sensitized particles comprising insoluble particles coated with a binding partner that specifically binds the analyte of interest. However, during the process of synthesizing such sensitized particles, it is difficult to control the amount of the binding partner that becomes bound to the particle. Therefore, while it is often desirable to know the concentration of the molecules that are immobilized on the particle, this concentration is often unknown. Accordingly, another aspect of this invention concerns a method of assaying sensitized particles to determine the concentration of a binding partner that is immobilized on an insoluble particle, comprising:

(a) incubating a solution of the sensitized particles having a first binding partner immobilized thereon with a known amount of a free fluorophore-labeled second binding partner attached to a fluorescent moiety, wherein the incubation is conducted under conditions that allow a complex formation between the immobilized first binding partner and the labeled second binding partner, whereby the fluorescence of the fluorophore moiety of the complex becomes quenched upon the formation of the complex;

(b) subjecting an amount of the incubated sample of step (a) to capillary electrophoresis; and (c) determining the amount of the first binding partner that is immobilized on the particle by detecting a laser-induced fluorescence of the free fluorophore-labeled second binding partner, wherein the laser-induced fluorescence is inversely proportional to the amount of first binding partner immobilized on the particle.

The methods of this invention can also be employed for simultaneously assaying a plurality of analytes in a sample.

Once fluorescence quenching is achieved according to the methods of this invention, the capillary electropherogram is simplified, thus eliminating the need to detect and separate the complex formed with the sensitized particles. This allows for the easy quantitation of the free (uncomplexed) fluorophore label.

Additional aspects, advantages and novel features of this invention shall be set forth in part in the description that follows, and in part, will become apparent to those skilled in the art upon examination of the following specification or may be learned by the practice of the invention. The invention is defined in its fullest scope in the appended claims and is described below in its preferred embodiments.

DESCRIPTION OF THE FIGURES

The accompanying drawings, which are incorporated herein and form a part of the specification, illustrate preferred embodiments of the present invention, and together with the description, serve to explain the principles of the inventions In the Figures.

DETAILED DESCRIPTION OF THE INVENTION

The method of this invention provides improved assays for the quantitation of an analyte of interest in a sample by providing particle-enhanced homogeneous assay formats that can be performed in conjunction with capillary electrophoresis and laser-induced fluorescence detection. The improved assays of this invention overcome the shortcomings of conventional assays described above by reducing the number of signals that must be separated and measured upon laser-induced fluorescence (LIF) of the assay reaction mixture. Consequently, the methods of this invention increase the accuracy of the detection and/or quantification of target analytes. The methods of this invention thus simplify the electropherograms obtained during CE-LIF. In accordance with the methods of this invention, it is possible to eliminate the need to separate the complexed labeled species from the uncomplexed labeled species during CE by quenching the signal of the fluorophore moiety on the complexed species.

Briefly, one aspect of the present invention provides improved competitive assays for determining the concentration of an analyte of interest in a sample. One preferred embodiment of such a competitive assay can be written generally, as shown in Equation 1:

$$\text{LX-(BP)}_x + \text{analyte*} + \text{analyte} \leftrightarrow \text{LX-(BP)}_x\text{-(analyte*)}_y + \text{LX-BP-(analyte)}_z + \text{analyte*} \quad (1)$$

where "LX-(BP)$_x$" represents a sensitized particle comprising an insoluble particle LX coated with a binding partner BP that specifically binds the analyte, "x" represents the number of binding partners immobilized on the insoluble particle, "analyte*" represents an analyte labeled with a fluorescent moiety, "y" represents the number of fluorophore-labeled analyte molecules that become bound to the sensitized particles (LX-BP) during the assay, and "z" represents the number of sample analyte molecules that become bound to the sensitized particles (LX-BP) during the assay. In the assay represented by Equation (1), the concentrations of the labeled analyte and the sensitized particles are fixed.

More specifically, one embodiment of a competitive assay of this invention as represented by Equation 1 comprises combining a sample which may contain the analyte of interest with a known amount of a free fluorophore-labeled analyte (analyte*) comprising the analyte attached to a fluorescent moiety and a known amount of sensitized particles (LX-BP) comprising a plurality of analyte-specific binding partners (BP) immobilized on an insoluble particle (LX) to form a reaction mixture. The reaction mixture is incubated under conditions that allow the formation of a first complex (LX-$(BP)_x$-(analyte*)$_y$) comprising a sensitized particle bound to the fluorophore-labeled analyte, and/or a second complex (LX-BP-(analyte)$_z$) comprising a sensitized particle bound to the sample analyte. Methods of preparing and incubating such reaction mixtures are well known to those skilled in the art and need not be described in further detail. Once a measurable reaction has proceeded, an amount of the incubated reaction mixture is then subjected to capillary electrophoresis. As described below in detail, the fluorescence of the fluorescent moiety becomes quenched upon the formation of the first complex. The concentration of the analyte is thus determined by detecting a laser-induced fluorescence of the remaining free fluorophore-labeled analyte (analyte*) present in the reaction mixture.

As used herein, the term "complex" refers to a complex that is formed upon the binding of an analyte with its specific binding partner.

As used herein, "binding pair member" or "binding member" refers to a member of a binding pair, i.e., two different molecules wherein one of the molecules specifically binds to the second molecule through a chemical or physical means. In addition to antigen and antibody binding pair members, other binding pairs include, as examples without limitation, biotin and avidin, carbohydrates and lectins, complementary nucleotide sequences, complementary peptide sequences, peptides and specific protein binders, enzyme cofactors and enzymes, and the like.

As used herein, the term "complexed fluorophore" refers to a fluorescent moiety that is attached to a compound (e.g., an analyte or a binding partner) that is part of a complex, wherein either the analyte or the binding partner is immobilized on an insoluble particle.

As used herein, the term "free fluorophore" refers to a fluorescent moiety that is attached to a compound (e.g., an analyte or a binding partner) that is not part of a complex.

As used herein, the term "sensitized particle" refers to an insoluble particle having either an analyte-specific binding partner or the analyte of interest immobilized thereon, where the binding partner or analyte is attached to the particle by covalent (chemical) bonds or by non-covalent bonds (e.g., physical adsorption). The insoluble particles may be any natural or synthetic material capable of having a binding partner or analyte immobilized thereon, provided that the particles can be suspended in solution as required for capillary electrophoresis. Examples of insoluble particles include, but are not limited to, polymers and copolymers of olefinically unsaturated monomers, such as polystyrene (also referred to as "latex"), acrylonitrile, polybutadiene, and derivatives and copolymers thereof (see, for example, Bangs, L. B., *Uniform Latex Particles*, (1984) and U.S. Pat. No. 4,305,925), charcoal, colloidal gold particles, glass, acrylamide, methacrylate, nylon, metals, metal oxides and their derivatives, dextran, cellulose and natural particle material, such as red blood cells, pollens, liposomes, and bacteria. In another embodiment, the insoluble particle may comprise a pre-coating of a fluorescence quencher, as discussed below in detail.

The term "binding partner," as used herein, refers to a molecule or substance that specifically recognizes and binds to a particular molecule or substance, such as an analyte of interest, and exhibits negligible cross-reactivity with other substances. Binding between an analyte and its specific binding partner may be via a chemical or physical means, such as by immunoreaction, complexation, and affinity binding. Typical binding partners include, but are not limited to, antigens, antigen fragments, receptors, nucleic acids, polyclonal and monoclonal antibodies and fragments, derivatives and complexes thereof cyclodextrans, crown ethers, lectins, binding proteins, such as protein A and protein G (to bind glycoproteins), bacteria, enzymes, avidin, streptavidin, intrinsic factor (eg., to bind vitamin $B_{12}$), folate-binding protein, and polypeptides, such as diacetyl-L-lysine-D-alanine-D-alanine, as described in copending and commonly assigned U.S. patent application Ser. No. 09/888,005 entitled "Homogeneous Assay of Vancomycin Using a Stable Particle-Vancomycin Conjugate, a Novel Rate Enhancer, and a Novel Dose Response Modulator", which is specifically incorporated herein by reference. Such binding partners specific for a given analyte may be obtained from commercial sources or may be prepared in accordance with standard procedures well known to those skilled in the art.

As will be discussed below in detail, in one embodiment, the fluorescence of a complexed fluorophore becomes self-quenched when a sufficient amount of the fluorophore moieties are close enough in proximity to each other such that energy transfer occurs between the fluorophore moieties. This is the situation that occurs when a sufficient amount of labeled analytes bind to sensitized particles to form the first complex (LX-$(BP)_x$-(analyte*)$_y$), as shown in Equation (1). Alternatively, fluorescence quenching can occur upon complex formation if the insoluble particle comprises a pre-coating of fluorescence quenchers. As a result of the quenching of the complexed fluorophore, the signal expected from the first complex does not appear in the electropherogram. Thus, the electropherogram obtained upon LIF detection contains substantially only the fluorescent signal produced from the free fluorophore-labeled analyte (analyte*). As a result, the electropherograms produced according to the methods of this invention are simplified and are easier to interpret compared to those obtained from conventional CE-LIF assays.

When the LIF detection is completed, the data obtained is compared with a standard curve prepared according to methods known to those skilled in the art to determine the original concentration of the analyte in the test sample. In the assay represented by Equation 1, the laser-induced fluorescence produced by the free fluorophore-labeled analyte is directly proportional to the concentration of the analyte present in the sample.

The method of the present invention also provides a time-saving advantage over conventional methods. That is, since the fluorescent signal produced by the first complex (LX-$(BP)_x$-(analyte*)$_y$) is quenched and therefore eliminated from the electropherogram, the method of this invention avoids the time-consuming optimization of CE parameters as required in conventional assays in order to achieve the complete separation of the free fluorophore-labeled analyte signal from the broad signal from the complexed label. Consequently, the method of this invention achieves a more accurate measurement of the analyte concentration and in a much shorter period of time as compared to conventional methods in which the complete separation of multiple signals, some of which are broad and overlap other signals, is necessary.

As stated above, fluorescence quenching according to this invention occurs due to at least one of the following conditions described below, i.e., by pre-coating the insoluble particle with fluorescence quenchers and/or self-quenching of the fluorophore moieties upon the complexation of a sufficient amount of fluorophore-labeled species to an insoluble particle.

1. Fluorescence Quenching Employing a Pre-Coated Particle.

In one embodiment of this invention, the insoluble particle is pre-coated with a fluorescence quencher prior to immobilizing a binding member onto the particle. In one embodiment, the fluorescence quencher is a fluorescence acceptor. A fluorescence acceptor is any compound or species which has an absorption band that overlaps with the emission band of the particular fluorescent label to be used in an assay. The acceptor can be selected from a group of compounds including, but not limited to, fluorescein derivatives and rhodamine derivatives. Other examples of fluorescent quenchers include, but are not limited to, heavy atoms, such as iodide, and metallic ions, such as $Co^{2+}$, $Ni^{2+}$, and $Cr^{3+}$.

The pre-coated particle is then loaded with an appropriate amount of a binding member. The procedures of pre-coating insoluble particles with fluorescence quenchers and the subsequent loading of the binding member onto the pre-coated particles are known to those skilled in the art.

When the immobilized first binding member complexes with the fluorescent-labeled second binding member, both the fluorescent label and the fluorescence quencher are brought into close proximity, since both species are now on the same particle. When the fluorescent label is irradiated, the energy can be transferred from the electronically excited state of the donor, i.e., the fluorescent label, to the fluorescence quencher. When the energy transfer is successful, the fluorescence intensity is either greatly diminished or completely quenched. The transfer efficiency depends not only on (1) the distance of the donor and quencher species, but also on (2) the fluorescence quantum yields of the donor, (3) the absorptivity of the quencher, (4) the integrated spectral overlap of the donor emission and quencher absorption as described above, and (5) the refractive index of the medium. The sensitized particle thus localizes both the fluorescence donor and quencher, and consequently renders fluorescence quenching possible because of their close proximity, which is necessary in order for fluorescence quenching to occur.

A well-known example of the fluorescence donor-acceptor system is the fluorescein-rhodamine system, in which the fluorescein is the donor and the rhodamine is the quencher. In this system, rhodamine has an absorption band (about 550 nm) which overlaps with the emission band of fluorescein (about 520 nm) (*Methods in Enzymology*, Vol. 74, Immunochemical Techniques, Part C, Section IA. "Fluorescence Immunoassay Methods", Langone and Van Vunakis, eds. 1981, Academic Press; *Fluorescence Spectroscopy. An Introduction for Biology and Medicine*. Pesce, Rosen and Pasby, eds., 1971, Marcel Dekker Inc., New York; Boguslaski, R. C. et al., *Appl. Biochem. and Biotechnology*. 7:401-414 (1982)).

Other examples of fluorescence donor and quenchers are the fluorescein-4',5'-dimethoxy-fluorescein—fluorescein pair (*Methods in Enzymology*, Vol. 74, Immunochemical Techniques, Part C, Section IA), earth metal chelate—Reactive Blue 4 pair (Youn, H. J., et. al., *Analytical Biochemistry*. 232:24-30 (1995)), the fluorescein-B—phycoerythrin pair and the B-phycoerythrin—Texas Red pair (Gosling, J. P., *Clin. Chem.* 36(8): 1408-1427 (1990)).

2. Fluorescence Quenching Without Pre-Coating the Insoluble Particle ("Self-Quenching").

Fluorescence quenching can also occur even without pre-coating the insoluble particle with a fluorescence quencher, provided that the loading of first binding members onto the particle is high, thus resulting in a high local concentration of the first binding member and hence a high local concentration of the labeled species onto each particle upon the complexation between the immobilized first binding member and the labeled second binding member.

When binding occurs between an immobilized first binding member and a fluorescent-labeled second binding member to form a complex, fluorescence quenching can occur upon such complex formation via dipole-dipole coupled energy transfer, provided that the particle is sufficiently loaded with first binding members. More specifically, a high loading on the particle means that the immobilized first binding members are in close proximity to each other on the particle. Consequently, when fluorescent-labeled second binding members become complexed to the immobilized first binding members, the fluorophore moieties are likewise in close proximity to each other. While not wanting to be bound by theory, it has been observed that if a sufficient amount of a fluorophore-labeled species complexes with an immobilized first binding member, the fluorescence of the fluorophore moiety becomes quenched and thus does not produce a peak in the electropherogram. That is, if a sufficient number of labeled second binding members are bound to a sensitized particle, the energy of the fluorescent moieties induced during LIF gets transferred between the immobilized labels (i.e., quenched) rather than to the detector to produce a detectable signal. Consequently, only the uncomplexed ("free") fluorophore-labeled species remaining in the reaction mixture produce a signal that is detected by LIF. As a result, the quenching efficiency is greatly enhanced.

The high loading of first binding members on the particles thus allows efficient self-quenching interactions between the complexed fluorescent labels as a result of (1) their high local concentration, (2) quenching interaction between a given label and the binding member to which it is bound as well as between the neighboring binding members, and (3) quenching interactions between the label and the surface of the particle. In fact, if the particle size is in the order of the wavelength of the fluorescent dye (e.g., 500 nm), the opaque particle can block the fluorescent label from the excitation light and similarly block the emitted light from reaching the detector, resulting in no detection of the fluorescence signal.

Accordingly, whether the methods of this invention utilize particles pre-coated with fluorescence quenchers or particles having a high loading of a binding member, a key feature of this invention is that the number of fluorophore-labeled species remaining in the assay reaction mixture that are detected by LIF after CE is reduced. Further, the detection of the uncomplexed labeled second binding pair member is simplified since the need to separate the complexed labeled species from the uncomplexed labeled species is eliminated.

An alternative embodiment of a competitive assay of this invention can be written generally, as shown in Equation 2:

$$LX\text{-}(analyte)_x + analyte + BP^* \leftrightarrow LX\text{-}(analyte)_x\text{-}(BP^*)_y + analyte\text{-}BP^* + BP^* \quad (2)$$

where "$LX\text{-}(analyte)_x$" represents a sensitized particle having "x" number of analyte molecules immobilized thereon, "$BP^*$" represents an analyte-specific binding partner labeled with a fluorescent moiety; "$LX\text{-}(analyte)_x\text{-}(BP^*)_y$" represents the complex formed upon binding between the immobilized analyte with "y" number of labeled binding partners, and "analyte-BP*" represents the complexed formed upon binding between the sample analyte and the labeled binding partner. In the assay represented by Equation (2), the concentrations of the labeled binding partner and the sensitized particles are fixed.

More specifically, in a competitive assay as represented by Equation 2, a sample which may contain the analyte of interest is combined with a fixed amount of sensitized particles comprising the analyte immobilized on insoluble particles and a fixed amount of an analyte-specific fluorophore-labeled binding partner (BP*). In this embodiment, a particle-immobilized analyte (LX-(analyte)$_x$) is allowed to compete with the sample analyte for binding to the labeled binding partner (BP*). The reaction mixture is incubated under conditions that allow the formation of a first complex (LX-(analyte)$_x$-(BP*)$_y$) comprising the immobilized analyte bound to a number of the labeled binding partners, and/or formation of a second complex (analyte-BP*) comprising the sample analyte bound to the fluorophore-labeled binding partner. Any conditions that will allow the formation of such complexes may be used in the methods of this invention and are well known to those skilled in the art.

Once a measurable reaction has proceeded as shown in Equation (2), an amount of the incubated reaction mixture is then subjected to capillary electrophoresis. In one embodiment of the assay, represented by Equation (2), the first complex comprises a sufficient amount of the labeled binding partner (BP*) such that the fluorophore labels are in close proximity. As a result, the fluorescence of the complexed fluorophore becomes quenched. In another embodiment of the assay, represented by Equation (2), the insoluble particle is pre-coated with a fluorescence quencher which quenches the fluorescence of the complexed fluorophore labels upon complex formation. In either case, the electropherogram obtained upon LIF detection will contain substantially only the fluorescent signals produced from the remaining free fluorophore-labeled binding partner (BP*) and the second complex (analyte-BP*).

Preferably, in the assay represented by Equation 2, the concentration of the analyte in the sample is determined by detecting a laser-induced fluorescence of the second complex (analyte-BP*) present in the reaction mixture, wherein the laser-induced fluorescence is directly proportional to the concentration of the analyte in the sample. Alternatively, the analyte concentration can be determined by detecting the fluorescence of the remaining free fluorophore-labeled binding partner (BP*), wherein the laser-induced fluorescence is inversely proportional to the concentration of the analyte in the sample.

Another aspect of this invention comprises a direct assay for determining the concentration of an analyte of interest in a sample. One embodiment of such a direct assay can be written generally, as shown in Equation 3:

$$LX\text{-}(BP_1)_x + \text{analyte} + BP_2^* \leftrightarrow LX\text{-}(BP_1)_x\text{-}(\text{analyte})_y\text{-}(BP_2^*)_z + BP_2^* + LX\text{-}(BP_1)_x \quad (3)$$

where "LX-(BP$_1$)$_x$" represents a sensitized particle comprising an insoluble particle LX coated with "x" number of first binding partners "BP$_1$" that specifically bind the analyte, "BP$_2$*" represents a free fluorophore-labeled binding partner comprising a second analyte-specific binding partner labeled with a fluorescent moiety, "LX-(BP$_1$)$_x$-(analyte)$_y$-(BP$_2$*)$_z$" represents a sandwich complex formed upon binding between the analyte and the first and second binding partners, "y" represents the number of analytes bound to the first binding partner, and "z" represents the number of fluorophore-labeled binding partners bound to the analyte. In the assay represented by Equation (3), the concentrations of the labeled binding partner and the sensitized particles are fixed.

In one embodiment of the assay represented by Equation (3), the first complex comprises a sufficient amount of the second labeled binding partner (BP$_2$*), such that the fluorophore labels are in close proximity. As a result, the fluorescence of the complexed fluorophore label becomes quenched. In another embodiment of the assay represented by Equation (3), the insoluble particle is pre-coated with a fluorescence quencher which quenches the fluorescence of the complexed fluorophore labels upon complex formation. In either case, in the direct assay represented by Equation (3), the electropherogram contains substantially only one signal, i.e., that produced by the free labeled binding partner (BP$_2$*), which is inversely proportional to the concentration of analyte in the sample.

To conduct the assays of the present invention, it is necessary to provide the sensitized particles. In one embodiment, the sensitized particles comprise carrier particles having bound thereto either a specific binding partner for the analyte or the analyte of interest. The binding partner or the analyte may be immobilized on the particles in accordance with standard techniques that are well known to those skilled in the art, such as physical (passive) absorption, facilitated (forced) absorption, and covalent coupling. For example, the binding partner or analyte may be covalently attached to the particle surface by modification with chemical functional groups capable of attaching the binding partner to the particle. See, for example, U.S. Pat. Nos. 4,064,080, 4,181,636, 4,210,723, 4,264,766, 4,521,521 and 4,305,925, all of which are specifically incorporated herein by reference. The techniques disclosed in these patents may be used to attach binding partners or analytes to the particles. See also Seaman, G. V. F., ed., *Latex Based Technology in Diagnostics, Health & Science Communications*, Washington, D.C. 20005 (1990), which is specifically incorporated herein by reference. Sensitized particles having the desired properties and characteristics may also be obtained commercially.

In another embodiment, the particle is first pre-coated with a fluorescence quencher prior to immobilizing the binding partner on its surface. When the fluorescence quencher is a fluorescence acceptor, the absorption wavelength of the acceptor is close to the emission wavelength of the fluorescent label to be utilized in the particular assay. The fluorescence acceptor is selected from a group of compounds having absorption bands overlapping with the emission band of the fluorescence label (donor) and includes fluorescein and rhodamine derivatives. Other examples of fluorescent quenchers include, but are not limited to, heavy atoms, such as iodide, and metallic ions, such as $Co^{2+}$, $Ni^{2+}$, and $Cr^{3+}$.

The pre-coated particle is then loaded with an appropriate amount of the binding partner for the analyte of interest. The procedures of pre-coating the quencher and the subsequent loading of the binding partner are known to those skilled in this art.

Examples of binding partners that can be immobilized on insoluble particles include avidin, streptavidin, lectins (e.g., concanavalin A to capture carbohydrates or glycoproteins), polyclonal antibodies, monoclonal antibodies, polypeptides (e.g., diacetyl-L-lysine-D-alanine-D-alanine to capture vancomycin), protein A and protein G (to capture glycoprotein), cyclodextrans (to capture small molecules into its cavity), crown ethers, intrinsic factor (to capture vitamin $B_{12}$), and folate-binding protein.

As discussed above, it is well known that in the preparation of such sensitized particles, it is impossible to control the amount of binding partner or analyte that becomes immobilized onto the insoluble particle. As a result, many of the particles prepared from the same lot will contain different amounts of the immobilized compound and will therefore bind to differing amounts of a specific binding partner in a particle-enhanced assay. However, it is often desirable to know the concentration of the compound that is immobilized on the insoluble particles. Accordingly, another aspect of this invention provides a method for quantitating the amount of molecules bound to insoluble particles. Such a method can be written generally, as shown in Equation 4:

$$\text{LX-(compound)}_x + \text{BP*} \leftrightarrow \text{LX-(compound)}_x\text{-(BP*)}_y + \text{BP*} \quad (4)$$

where "LX-(compound)$_x$" represents a sensitized particle having "x" number of compound molecules immobilized thereon, "BP*" is a fluorophore-labeled binding partner for the compound, and "LX-(compound)$_x$-(BP*)$_y$," is the complex formed upon binding between the compound and the binding partner. In the method represented by Equation 4, a fixed amount of the sensitized particles are combined with a fixed amount of the fluorophore-labeled binding partner to form a reaction mixture. The reaction mixture is incubated under conditions that allow the formation of the complex.

In one embodiment of the assay represented by Equation (4), the complex comprises a sufficient amount of the labeled binding partner (BP*), such that the fluorophore labels are in close proximity. As a result, the fluorescence of the complexed fluorophore becomes quenched. In another embodiment of the assay represented by Equation (4), the insoluble particle is pre-coated with a fluorescence quencher which quenches the fluorescence of the completed fluorophore labels upon complex formation. When the fluorescence of the labeled binding partner (BP*) that is part of the complex LX-(compound)$_x$-(BP*)$_y$ becomes quenched, the only signal substantially detected in the electropherogram is that produced by the free labeled binding partner (BP*). With this method, the quantitation of immobilized compound may be determined at a fixed label concentration (BP*) or at a fixed sensitized particle (LX-(compound)$_x$) concentration. In either case, the fluorescence signal of the label is inversely proportional to the concentration of the compound bound to the insoluble particles.

One specific example of the assay represented by Equation 4 is directed towards the quantitation of sensitized particles comprising avidin bound to latex particles of sub-micron range. Avidin-coated latex particles are a key intermediate for the preparation of bidentate conjugates for the Synchron CX®, Synchron LX®, and Immage® (see U.S. Pat. Nos. 5,747,352, 5,422,281, and 5,196,351, which are specifically incorporated herein by reference). Current methods used for evaluating these latex-avidin particles are labor intensive and time-consuming. Conventional methods include the preparation of a small amount of a bidentate conjugate by coupling the latex-avidin particles with a bidentate, followed by the evaluation of the conjugate for acceptable immunoreactivity on a Synchron® system. In contrast, the CE-LIF method of the present invention as represented by Equation 4 directly tests the latex-avidin particles, and therefore is much simpler and faster than conventional methods, thus reducing the testing time by 3 to 10 days. The method according to Equation 4 involves incubating the latex-avidin particles with a known amount of free biotin-fluorescein, performing CE on an aliquot, and detecting laser-induced fluorescence of remaining free biotin-fluorescein in the reaction mixture. The electropherogram is easy to interpret and contains mainly the free label, since fluorescence is highly quenched upon the complexation of the biotin-fluorescein with the latex-avidin. Each electropherogram can be obtained in less than 3.5 minutes.

The method of this invention is also suitable for the simultaneous and homogeneous detection of multiple target analytes in a sample utilizing a particle-enhanced assay format in conjunction with CE. In accordance with one embodiment of the present invention, such a method, which is similar to the competitive assay described in Equation 1, can be written generally, as shown in Equation 5:

$$\begin{aligned}
\text{BP}_1\text{-LX-BP}_2 + \text{AN}_1 + \text{AN}_1^* + \text{AN}_2 + \text{AN}_2^{**} &\leftrightarrow [\text{AN}_1^*\text{-}(\text{BP}_1\text{-LX-BP}_2)\text{-AN}_2^{**}] + [\text{AN}_1\text{-}(\text{BP}_1\text{-LX-BP}_2)\text{-} \\
&\text{AN}_2^{**}] + [\text{AN}_1^*\text{-}(\text{BP}_1\text{-LX-BP}_2)\text{-AN}_2] + [\text{AN}_1\text{-} \\
&(\text{BP}_1\text{-LX-BP}_2)\text{-AN}_2] + [\text{AN}_1^*\text{-}(\text{BP}_1\text{-LX-BP}_2)] + \\
&[\text{AN}_1\text{-}(\text{BP}_1\text{-LX-BP}_2)] + [(\text{BP}_1\text{-LX-BP}_2)\text{-AN}_2^{**}] + \\
&[(\text{BP}_1\text{-LX-BP}_2)\text{-AN}_2] + \text{AN}_1^* + \text{AN}_2^{**}
\end{aligned} \quad (5)$$

where "BP$_1$-LX-BP$_2$" represents an insoluble particle coated with both a first binding partner "BP$_1$" specific for a first sample analyte and a second binding partner "BP$_2$" specific for a second sample analyte, "AN$_1$" is the first sample analyte, "AN$_1$*" is a first sample analyte labeled with a fluorescent moiety, "AN$_2$" is the second sample analyte, and "AN$_2$**" is a second sample analyte labeled with a fluorescent moiety. In the assay represented by Equation (4), the concentrations of the labeled sample analytes and the sensitized particles are fixed.

The multiple analyte assay is performed in a manner similar to that described above for competitive assays. Thus, the reaction mixture is incubated under conditions that allow the formation of a first complex [AN$_1$*-(BP$_1$-LX-BP$_2$)-AN$_2$] comprising the sensitized particles bound to the first labeled analyte and the second labeled analyte, and/or a second complex [AN$_1$-(BP$_1$-LX-BP$_2$)-AN$_2$] comprising the sensitized particles bound to the first sample analyte and the second labeled analyte, and/or a third complex [AN$_1$*-(BP$_1$-LX-BP$_2$)-AN$_2$] comprising the sensitized particles bound to the first labeled analyte and the second sample analyte, and/or a fourth complex [AN$_1$-(BP$_1$-LX-BP$_2$)-AN$_2$] comprising the sensitized particle bound to the first sample analyte and the second sample analyte, and/or a fifth complex [AN$_1$*-(BP$_1$-LX-BP$_2$)] comprising the sensitized particles bound to the first labeled analyte, and/or a sixth complex [AN$_1$-(BP$_1$-LX-BP$_2$)] comprising the sensitized particles bound to the first sample analyte, and/or a seventh complex [(BP$_1$-LX-BP$_2$)-AN$_2$**] comprising the sensitized particle bound to the second labeled analyte, and/or an eight complex [(BP$_1$-LX-BP$_2$)-AN$_2$] comprising the sensitized particles bound to the second sample analyte. The reaction mixture is then subjected to CE and analyzed by LIF. Even though the reaction mixture contains multiple products, the electropherogram still contains only two signals, i.e., from the free first and second labeled analytes AN$_1$* and AN$_2$**, since the fluorescence of all of the various complexed forms of the first and second labeled analytes (i.e., the first, second, third, fifth, and seventh complexes) is quenched upon the formation of the complexes. Such quenching will occur if the complexed fluorophores are in close proximity, or if the particle is pre-coated with fluorescence quenching molecules, as described above.

If it is possible to separate the free first and second labeled analytes AN$_1$* and AN$_2$**, respectively, during CE, the first and second analytes may be labeled with the same fluorescent moiety. However, if the signals from the free first and second labeled analytes are fairly close, it is preferred that each analyte be labeled with a different fluorescent moiety.

The methods of the present invention are fundamentally different from known procedures. In conventional assays employing CE-LIF as a means of analyte quantitation, signals from all of the labeled species in the assay reaction mixture must be sufficiently separated in order to accurately measure the various signals in the electropherogram. However, even conventional assays employing particle-enhanced assay formats are not able to achieve sufficient separation and, thus, accurate measurement of analyte concentration. This is due to the fact that it is difficult to control the concentration of the molecules that become immobilized on the insoluble particle during the preparation of sensitized particles. Complexes formed during particle-enhanced assays using sensitized particles that are coated with varying concentrations of molecules will migrate at varying rates during CE, thus producing a broad peak in the electropherogram which is difficult to resolve and which often overlaps with one or more other peaks in the electropherogram. The methods of this invention alleviate this problem by causing the broad peak produced from complexed fluorophore-labeled moieties to become quenched, thus producing a cleaner and simpler electropherogram, which consequently provides a more accurate determination of analyte concentration.

The methods of this invention are suitable for determining the concentration of an analyte of interest in a variety of samples. Typical samples include, but are not limited to, clinical samples, such as whole blood, milk, serum, plasma, urine, cerebrospinal fluid, etc., water, waste, foodstuffs, proteins, and drug substances, such as purified drugs, etc.

Any of a wide variety of analytes may be evaluated in accordance with the methods of the present invention. As used herein, an "analyte" refers to the substance whose presence and/or concentration in a sample is to be determined. The term "analyte" refers to any substance for which there exists a specific binding partner, or for which a specific binding member can be prepared, and which will bind the specific binding member in an assay. Representative analytes include, but are not limited to, antigens, haptens, antibodies, proteins (such as immunoglobulins, receptors, enzymes, etc.), peptides, amino acids, hormones, steroids, glycoproteins, carbohydrates, cancer cell markers, tissue cells, viruses, vitamins, drugs, metabolites, nucleic acids, and pesticides, substances of abuse (such as cocaine, cannabinoids, opiates, etc.), toxins, pharmacological agents, etc.). The methods of the present invention are particularly suitable for analyzing proteins, drugs and other pharmacological agents.

The term "antibody," as used herein, refers to immunoglobulins that are produced in response to the detection of a foreign substance, and includes intact molecules as well as functional fragments thereof, such as Fab, $F(ab')_2$, and Fv. Most preferably, the antibody molecules used will be purified monoclonal antibodies, preferably with affinity constants of $10^9$ or more. In lieu of such antibody molecules, polyclonal antibodies, Fab or $F(ab)_2$ fragments, single chain antibodies, or solubilized receptors or receptor ligands can be employed.

The fluorophore label used in conjunction with the above embodiments is a fluorescent moiety. Suitable fluorophores include, but are not limited to, fluorescein, isothiocyanate, rhodamine, phycoerythrin, phycocyanin, allophycocyanin, ophthaldehyde label, fluorescamine, tetramethylrhodamine, dipyrromethenboron difluoride dyes (BODIPY®; Molecular Probes, Inc.), near infrared dyes, lanthanide chelates, or analytes bearing such fluorescent moieties. Where the labeling of an antibody is desired, fluorescein labels may preferably be used. Such a labeled antibody may be used in direct immunoassays for protein species present at concentrations of approximately $10^{-10}$ molar. Any suitable method known to those skilled in the art ay be used to directly label the analytes of binding partners of the present invention.

Once the assay reaction has occurred, the reactants and products are subjected to CE under conditions sufficient to resolve uncompleted ("free") labeled species but which need not be optimized to resolve the complexed fluorophore-labeled species. The CE separation technique for proteins provides a means to separate the free labeled species without the use of a solid support. The application of these separation techniques in conjunction with laser-induced fluorescence detection make possible the homogeneous immunochemical measurement of species at concentrations in the range of $10^{-9}$ to $10^{-10}$ molar, as described in U.S. Pat. No. 5,571,080, which is specifically incorporated herein by reference.

Normal CE can be separated generally into two categories based upon the contents of the capillary columns. In "fixed gel" CE, the capillary tube is filled with a suitable gel, e.g., polyacrylamide gel, and the separation of the constituents of the sample is thus predicated by both the size and the charge of the constituents. Despite the speed of analysis, fixed gel CE has several disadvantages, notably, the unpredictability and non-durable nature of the gel material. These factors make fixed gel CE unacceptable in any setting where numerous analytical runs are conducted.

In the second form of CE (i.e., "open" CE), the capillary tube is filled with an electrically conductive buffer solution (Kim, J. W. et al., *Clin. Chem.* 39:689-692 (1993)). Most preferably, the buffer is 150 mM borate, pH 10.00+/−0.25; concentrations between about 70 mM and about 400 mM are, however, viable. As the molarity of the buffer increases, the temperature inside the column can increase, and thus, in situations where temperature effects upon the constituents are a factor, lower concentrations of the buffer should be utilized. However, it is to be understood that the disclosed protocol can be accomplished with any separation buffer used in conjunction with the separation of proteinaceous materials using coated or untreated columns.

The capillary tube is then ionized with a negative charge. Such ionization causes the capillary wall to become negatively charged, thereby attracting positive ions from the buffer. Because the electroneutrality of the solution must be maintained, any flow of positive ions towards the capillary wall will be accompanied by a similar movement of the buffer solution and the constituents of the sample. This electroosmotic flow provides a fixed velocity component which drives both neutral species and ionic species, regardless of charge, towards the cathode. The buffer in "open CE" is stable against conduction and diffusion. Accordingly, separations can be obtained in "open CE" that are quite similar to those obtained in gel-based electrophoresis.

Open CE has many desirable qualities for, e.g., clinical sample analysis, such as: (1) since the analysis does not involve a gel-filled column, the inherent limitations on the number of analytical runs that can be conducted with any particular gel-filled column are avoided; (2) when the capillary column is untreated, the aura of unpredictability which can be associated with coated columns is avoided; the sample size is small (usually on the order of 5 to 200 µL of diluted sample); (3) sample analysis time is fast i.e., less than about 20 minutes; and (4) the protocol lends itself to automation, thus decreasing the labor skills necessary for efficient and effective sample analysis. The capillary column may be coated on the outside (using, e.g., a polyimide material) for ease of handling.

While the methods of the present invention can use either untreated or coated columns, it is preferred that the columns be untreated. When untreated capillary columns are utilized, preferably the separation buffer is as disclosed in U.S. Pat. No. 5,120,413, herein incorporated by reference. Suitable columns are further disclosed by Guttman, A., U.S. Pat. No. 5,213,669; Burolla, V. P., U.S. Pat. No. 5,198,091; Shieh, C.-H., U.S. Pat. No. 5,098,539; each of which is incorporated herein by reference.

The presence of the label is preferably determined by automated or semi-automated means. In the preferred embodiment, the detection is mediated using a laser-induced fluorescence ("LIF") detector. An exemplary detector would contain a 1-3 milliwatt helium neon laser (543.5 nm) suitable for exciting the fluorophore. A suitable 2.5 milliwatt green helium-neon laser emitting at 543.5 nm is available from Particle Measuring Systems, Boulder, Colo. The laser output is preferably filtered using a laser line filter and is focused into the detection region of the separation capillary. In a preferred embodiment, the detection system will be integrated into the P/ACE® system (Beckman Instruments, Inc.) using a laser head coupler to a standard SMA-905 fiber connector to the P/ACE® system with LIF detector (available from OZ Optics, Ontario, Canada). The fluorescent emission is preferably collected and collimated using a parabolic reflector which holds the capillary at its focus, and a scatter mask is preferably placed across the front of the parabola in the plane of intense laser scatter. The collimated emission is passed first through a notch filter (543.5 nm blocking), then through a 9 nm band pass filter centered at 580 nm (such filters are available from Barr Associates, Westford, Mass. and from Oriel, Stratford, Conn.). Detection is preferably accomplished using an end-on type photomultiplier tube, such as R374, Hamamatsu.

Capillary electrophoresis instrumentation systems that can be used in conjunction with the present invention are well known. A particularly preferred instrument is a multi-channel apparatus that allows the simultaneous evaluation of at least two different aliquots of sample; more preferably, the apparatus has the capability of analyzing several aliquots simultaneously such that multiple electropherograms can be obtained and compared. A particularly preferred capillary electrophoretic system is disclosed in U.S. Pat. No. 5,413,686, which is incorporated herein by reference.

A particularly preferred capillary electrophoretic system is the P/ACE® high performance capillary electrophoresis system (Beckman Instruments, Inc.) (Chen, F-T. A., *Clin. Chem.* 38:1651-1953 (1992); Chen, F-T. A., *J Chromatogr.* 559:445-453 (1991); Fu, P. C. et al., *Clin. Chem.* 37:970 (1991); Chen, F-T. A., *Clin. Chem.* 37:1061 (199); Gordon, M. J. et al., *Anal. Chem.* 63:69-72 (1991), all incorporated herein by reference). Such instruments are most preferred in that normalization of the electropherograms can be accomplished via on-board computer software, such as System Gold® software (Beckman Instruments, Inc., Fullerton, Calif., USA).

The evaluation of CE is typically visually oriented, i.e., the electropherograms of samples are evaluated to determine the presence of peaks. The areas beneath a peak correspond to the concentration of the analyte being assayed. Typically, the electropherogram is derived by plotting detection units, such as fluorescence, on the vertical axis, and the time of constituent traversal through the column to a detection region on the horizontal axis. Results can also be derived in terns of a unit value, typically derived from the areas bounded by the individual peaks.

EXAMPLES

In the examples below, commercially available biotin-fluorescein was used as the detection label, and is commercially available. Latex particle was of the carboxylate-modified type and had a diameter of about 60 nm. The methods involved mixing the biotin-fluorescein label with latex-avidin, followed by monitoring the fluorescence signal of the free label on a Beckman P/ACE® system, which was equipped with a LIF detector with the excitation at 488 nm and the emission at 520 nm. The entire in-process testing can be completed in less than two hours. Each electropherogram was obtained in less than 3.5 minutes, and consisted mainly of the free label. Because of extensive fluorescence quenching of the bound biotin-fluorescein, latex-avidin-biotin fluorescein was hardly visible, except at high concentrations. With this method, functional avidin quantitation could be determined at a fixed label concentration or a fixed latex-avidin concentration. In either case, the fluorescence signal of the label was inversely proportional to the concentration of the latex-immobilized avidin below the avidin saturation point. At the avidin saturation point, the functional amount of avidin in terms of biotin-binding capacity on the latex particle could be derived from a known concentration of biotin-fluorescein label.

The examples below illustrate a CE-LIF method of this invention for quantifying the functional avidin concentration from the following latex-avidin materials: (1) Lot M602100, using reactant weight ratio of 0.35 for avidin to carboxylate-modified latex particle (or an A/C ratio of 0.35), and (2) Lots 365R and KP1, employing two different batches of latex particles and the same batch of avidin, and using an A/C ratio of 0.15. As shown by the results, a higher A/C ratio led to higher avidin loading as anticipated. However, the two qualified latex particles used to prepare the second and third lots were observed to result in as much as a 60% difference in avidin loading, even when the same avidin material was used.

Reagents and Buffers:

Latex-avidin materials (A/C ratio 0.35), Lot M602100 (A/C ratio 0.35), and Lots 365R and KP1 (A/C ratio 0.15) were prepared in-house.

Biotin-fluorescein, 5-((N-(5-(N-(6-(biotinoyl)amino)hexanoyl)amino)pentyl) thioureidyl fluorescein, was purchased from Molecular Probe. Two different vials of the same lot were purchased. One vial was utilized to assess the in-house latex-avidin material. Before use, the biotin-fluorescein was standardized by CE-LIF against a known concentration of streptavidin, which, in turn, was quantitated with HABA on DU-70. Another vial was employed without standardization in the testing of the remaining latex-avidin materials.

GTS buffer: GTS was the CE running buffer, and consisted of 192 mM glycine, 25 mM TRIS, and 50 mM sodium chloride at pH 8.3.

GTB buffer: GTB buffer was used as the diluent for the latex materials, as well as the biotin-fluorescein label. It was formulated to contain 192 mM glycine, 25 mM TRIS, and 0.15% BSA at pH 8.3.

Capillary Electrophoresis Using LIF Detection:

Capillary electrophoresis experiments were conducted on a P/ACE® system equipped with LIF detection. The excitation wavelength was 490 nm, and the emission wavelength was 520 nm. Analysis was performed on an uncoated fused-silica capillary with a dimension of 50 μm i.d. and a 20 cm separation length (27 cm total length). The applied voltage was 10 kV. The sample injection time was 2 seconds. GTS was used as the separation buffer. Current observed ranged from 45 to 55 μA.

Assay Protocol:

Latex-avidin and biotin-fluorescein reagents were mixed according to the following protocol, allowed to incubate for at least 2 minutes, and analyzed by CE-LIF: 100 µL GTB buffer, 100 µL latex-avidin diluted in GTB buffer, or 100 µL GTB buffer only as reference, and 100 µL biotin-fluorescein at $3\times10^{-7}$ M or $3.68\times10^{-8}$ M in GTB buffer.

Figure 1:
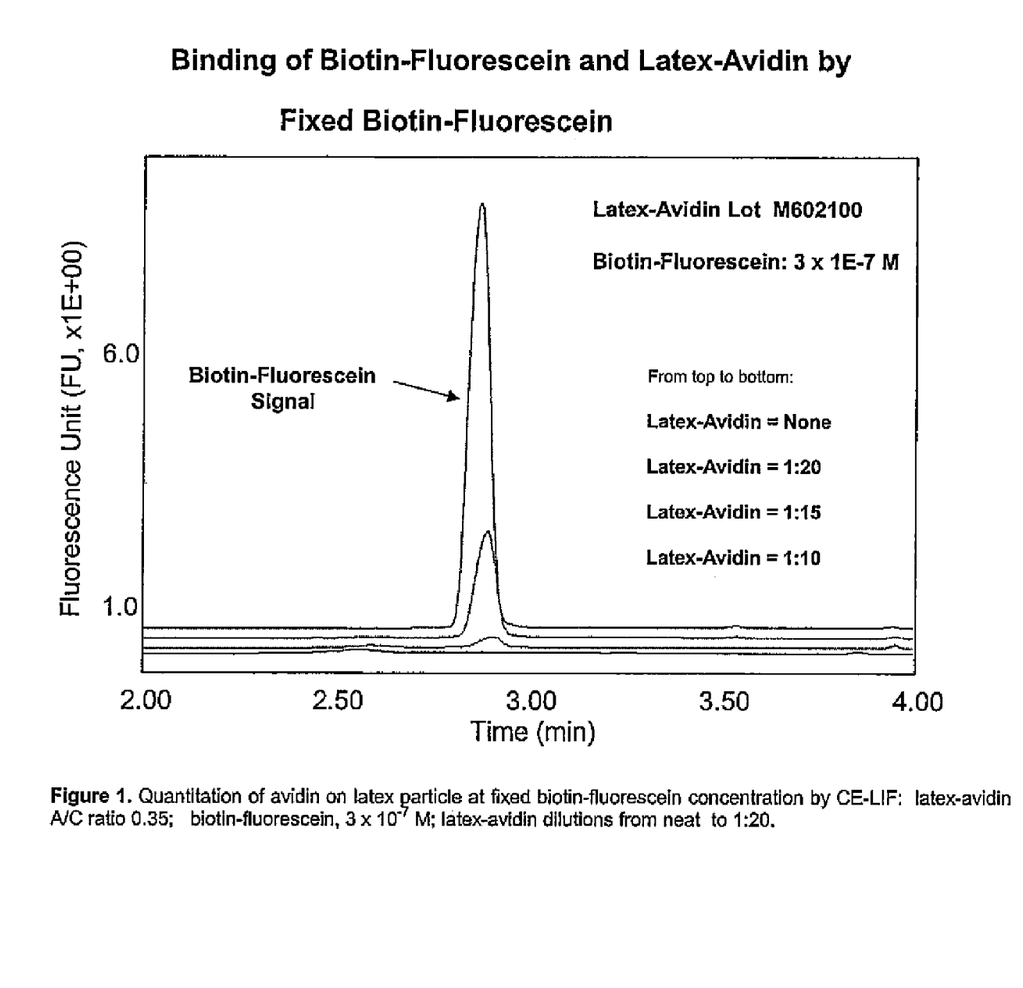
FIG. 1 shows a series of electropherograms showing the quantitation of a first lot of avidin-coated latex particles at a fixed biotin-fluorescein concentration by CE-LIF with various dilutions of the particles.

Results:

Quantitation of Latex-Avidin (Lot M602100, A/C Ratio 0.35) Using Fixed Biotin-Fluorescein at $3\times10^{-7}$ M Samples of latex-avidin at various dilutions were prepared and allowed to react with biotin-fluorescein at $3\times10^{-7}$ M. As shown in FIG. 1, a latex-avidin dilution of about 1:12.5 was required to consume all the biotin label. This amount was equivalent to $1\times12.5\times3\times10^{-7}$ M, or $3.75\times10^{-6}$ M, biotin-binding capacity in the undiluted latex-avidin material.

Quantitation of Latex-Avidin (Lot M602100, A/C Ratio 0.35) at Fixed Latex-Avidin Dilution of 1:100

Figure 2:
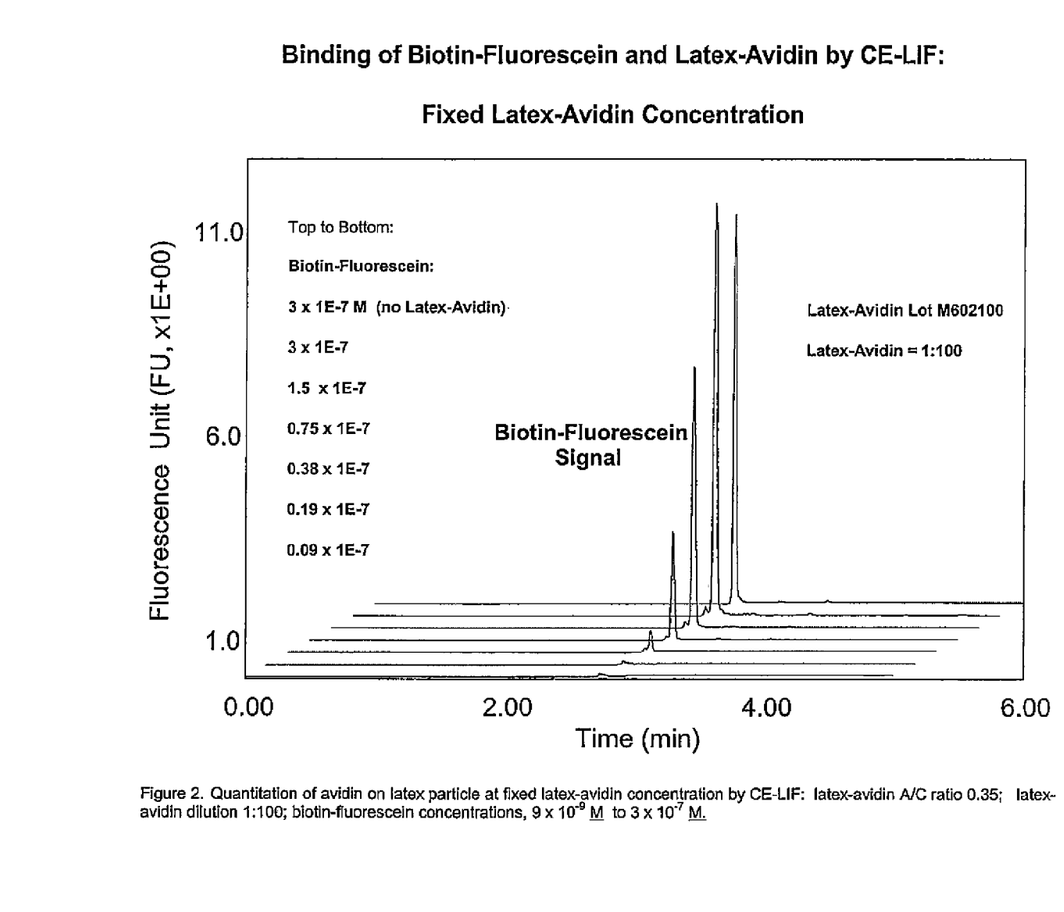
FIG. 2 shows a series of electropherograms showing the quantitation of a first lot of avidin-coated latex particles at two biotin-fluorescein concentrations by CE-LIF.

FIG. 2 summarizes the results of the reaction between latex-avidin at a fixed concentration (1:100) and biotin-fluorescein at concentrations ranging from $9\times10^{-9}$ M to $3\times10^{-7}$ M. As the results indicated, a saturation point for avidin was reached at a biotin-fluorescein concentration of about $0.35\times10^{-7}$ M. This translated into a functional avidin concentration equivalent to $100\times0.35\times10^{-7}$ M, or $3.5\times10^{-7}$ M, biotin-binding sites for the undiluted latex-avidin material, in close agreement with the results determined above using a fixed amount of biotin-fluorescein.

Comparison of Two Lots of Latex-Avidin (Lot 365R and Lot KP1, A/C Ratio 0.15) Using Biotin-Fluorescein at $3.68\times10^{-8}$ M In the manufacturing of latex-avidin-bidentate reagent using a new lot of latex particle, it was found that the conjugate reagent exhibited much lower immunoreactivity on the Synchron as compared to a reference reagent prepared using a previous lot of latex. To validate the CE method disclosed in this invention, we obtained and evaluated the two latex-avidin intermediates.

Figure 3:
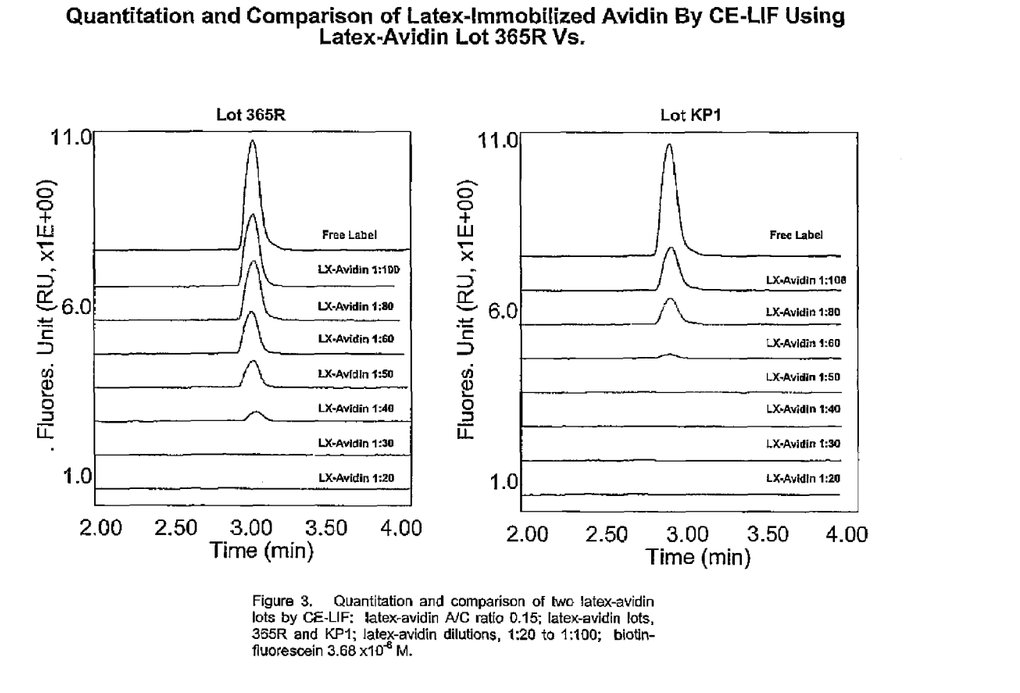
FIG. 3 shows a series of electropherograms for two different lots of avidin-coated latex particles at a fixed biotin-fluorescein concentration by CE-LIF with various dilutions of the particles.

Results are presented in FIG. 3. The amount of functional avidin immobilized on the old latex lot (KP1) corresponded to 1:60 titer at the avidin saturation point, i.e., $60\times3.68\times10^{-8}$ M, or $2.2\times10^{-6}$ M, equivalent of biotin for the undiluted latex-avidin material. This amount was 1.7 times higher than the material generated from the new latex lot (Lot 365R), which exhibited a corresponding titer of only 1:35, or $35\times3.68\times10^{-8}$ M, or $1.3\times10^{-6}$ M, equivalent of biotin. The CE-LIF results were consistent with those obtained from immunoassays, which indicated a difference of 60% in immunoreactivity from the respective latex-avidin-bidentate conjugates evaluated on the Synchron CX® system.

The invention may be embodied in other specific forms without departing from its essential characteristics. The described embodiments are to be considered in all respects only as illustrative and not as restrictive. Indeed, those skilled in the art can readily envision and produce further embodiments, based on the teachings herein, without undue experimentation. The scope of the invention is, therefore, indicated by the appended claims rather than by the foregoing description. All changes that come Within the meaning and range of the equivalence of the claims are to be embraced within their scope.

What is claimed is:

1. A method of assaying the concentration of an analyte in a sample, comprising:
    (a) providing sensitized particles comprising a first analyte-specific binding partner immobilized thereon;
    (b) providing a free fluorophore-labeled binding partner comprising a second analyte-specific binding partner labeled with a fluorescent moiety;
    (c) incubating said sample with a known amount of said sensitized particles and a known amount of said fluorophore-labeled binding partner under conditions that allow formation of a sandwich complex comprising said analyte bound to said immobilized first binding partner and to said labeled binding partner, whereby the fluorescence of said fluorophore moiety of said sandwich complex is quenched upon formation of said sandwich complex;
    (d) subjecting an amount of said incubated sample of step (c) to capillary electrophoresis under conditions that do not require separation of said sandwich complex and said free fluorophore-labeled binding partner that is not bound during incubation; and
    (e) determining the concentration of said analyte by detecting a laser-induced fluorescence of said free fluorophore-labeled binding partner that is not bound during incubation, wherein said laser-induced fluorescence is inversely proportional to the concentration of said analyte in said sample.

2. The method of claim 1, wherein said sensitized particles further comprise a coating of fluorescence quenchers.

3. The method of claim 2, wherein said fluorescence quenchers are selected from the group consisting of fluorescein derivatives, rhodamine derivatives, heavy atoms, iodide, $Co^{2+}$, $Ni^{2+}$, and $Cr^{3+}$.

4. The method of claim 1, wherein said analyte is selected from the group consisting of antigens, haptens, antibodies, proteins, glycoproteins, carbohydrates, immunoglobulins, receptors, enzymes, peptides, amino acids, hormones, steroids, cancer cell markers, tissue cells, viruses, vitamins, drugs, metabolites, nucleic acids, pesticides and toxins.

5. The method of claim 1, wherein said first binding partner is selected from the group consisting of antigens, antigen fragments, receptors, nucleic acids, and polyclonal and monoclonal antibodies and fragments, derivatives and complexes thereof, lectins, protein A, protein G, polypeptides, avidin, streptavidin, cyclodextrans, and crown ethers, intrinsic factor, and folate binding protein.

6. The method of claim 1, wherein said second binding partner is selected from the group consisting of antigens, antigen fragments, receptors, nucleic acids, and polyclonal and monoclonal antibodies and fragments, derivatives and complexes thereof.

7. The method of claim 1, wherein said sample is selected from the group consisting of whole blood, serum, plasma, urine, cerebrospinal fluid, milk, water, foodstuffs, protein and drug.

8. The method of claim 1, wherein said particle is selected from the group consisting of polymers and copolymers of olefinically unsaturated monomers, glass, acrylamide, methacrylate, nylon, metals, metal oxides and their derivatives, dextran, cellulose, red blood cells, pollens, liposomes and bacteria.

9. The method of claim 1, wherein said fluorescent moiety is selected from the group consisting of fluorescein, isothiocyanate, rhodamine, phycoerythrin, phycocyanin, allophycocyanin, ophthaldehyde label, fluorescamine, tetramethylrhodamine, dipyrromethene boron difluoride dyes, near infrared dyes and lanthanide chelates.

10. The method of claim 1, wherein in step (d), said capillary electrophoresis is conducted in a fused silica column.

* * * * *